US012429404B1

(12) United States Patent
Zhong et al.

(10) Patent No.: US 12,429,404 B1
(45) Date of Patent: Sep. 30, 2025

(54) SEMICONDUCTOR LOW-TEMPERATURE ELEMENTAL MERCURY GENERATOR

(71) Applicants: HUANENG CHONGQING LUOHUANG POWER GENERATION CO., LTD., Luohuang (CN); BEIJING HUANENG CHANGJIANG ENVIRONMENTAL PROTECTION TECHNOLOGY RESEARCH INSTITUTE CO., LTD., Beijing (CN)

(72) Inventors: Li Zhong, Chongqing (CN); Lipeng Han, Chongqing (CN); Chen Guo, Chongqing (CN); Xun Wu, Chongqing (CN); Duo Zeng, Chongqing (CN); Nan Li, Chongqing (CN); Yanxuan Liang, Chongqing (CN); Wanjie Wang, Chongqing (CN)

(73) Assignees: HUANENG CHONGQING LUOHUANG POWER GENERATION CO., LTD., Chongqing (CN); BEIJING HUANENG CHANGJIANG ENVIRONMENTAL PROTECTION TECHNOLOGY RESEARCH INSTITUTE CO., LTD, Beijing (CN)

( * ) Notice: Subject to any disclaimer, the term of this patent is extended or adjusted under 35 U.S.C. 154(b) by 0 days.

(21) Appl. No.: 19/262,135

(22) Filed: Jul. 8, 2025

Related U.S. Application Data

(63) Continuation of application No. PCT/CN2024/099272, filed on Jun. 14, 2024.

(51) Int. Cl.
*G01N 1/38* (2006.01)
*G01N 33/00* (2006.01)

(52) U.S. Cl.
CPC .......... *G01N 1/38* (2013.01); *G01N 33/0045* (2013.01); *G01N 2001/383* (2013.01); *G01N 2001/386* (2013.01)

(58) Field of Classification Search
CPC ................. G01N 1/38; G01N 33/0045; G01N 2001/383; G01N 2001/386
See application file for complete search history.

(56) References Cited

U.S. PATENT DOCUMENTS

| 2004/0151622 A1* | 8/2004 | Tseng | G01N 21/6404 422/52 |
| 2014/0106461 A1* | 4/2014 | Gunther | G01N 33/2025 422/78 |

FOREIGN PATENT DOCUMENTS

| CN | 1502398 A | 6/2004 |
| CN | 102253168 A | 11/2011 |

(Continued)

OTHER PUBLICATIONS

English Machine Translation of CN-106525554-A (Year: 2017).*

(Continued)

*Primary Examiner* — David Z Huang
(74) *Attorney, Agent, or Firm* — Ming Jiang; OPENPTO US LLC

(57) ABSTRACT

A semiconductor low-temperature elemental mercury generator is provided, and includes a gas source and a mercury pool generating chamber, the gas source is communicated with a carrier gas pipeline and a dilution gas pipeline. The mercury pool generating chamber includes a semiconductor refrigeration device, a gas mixing device and a coil, the coil is kept at a constant temperature through the semiconductor refrigeration device, the carrier gas pipeline is communicated with the coil, and the gas mixing device is communicated with a gas outlet of the coil and the dilution gas pipeline. The semiconductor low-temperature elemental (Continued)

mercury generator has the advantages of simple operation and accurate mercury standard gas concentration.

7 Claims, 1 Drawing Sheet

(56)  References Cited

FOREIGN PATENT DOCUMENTS

| | | | | |
|---|---|---|---|---|
| CN | 202661381 U | 1/2013 | | |
| CN | 101980013 B | 7/2013 | | |
| CN | 103335913 A | 10/2013 | | |
| CN | 102253168 B | 1/2014 | | |
| CN | 103721640 A | 4/2014 | | |
| CN | 105699146 A | 6/2016 | | |
| CN | 106525554 A | * 3/2017 | ............... | G01N 1/38 |
| CN | 109596546 A | 4/2019 | | |
| CN | 110052225 A | 7/2019 | | |
| CN | 216117490 U | 3/2022 | | |
| CN | 116008024 A | 4/2023 | | |
| CN | 116773299 A | 9/2023 | | |
| CN | 220019106 U | 11/2023 | | |
| DE | 4131811 A1 | 3/1992 | | |

OTHER PUBLICATIONS

Eaching and Research Section of Metallurgical Principles, Central South Institute of Mining and Metallurgy,Principles of Colored Metallurgy,Journal,Sep. 30, 1961,p. 35,China Industrial Plate Society.

* cited by examiner

SEMICONDUCTOR LOW-TEMPERATURE ELEMENTAL MERCURY GENERATOR

CROSS-REFERENCE TO RELATED APPLICATIONS

This application is a continuation of PCT/CN2024/099272, filed on Jun. 14, 2024 and claims priority of Chinese Patent Application No. 202310713445.3, filed on Jun. 15, 2023, the contents of which are hereby incorporated by reference.

TECHNICAL FIELD

The disclosure relates to the technical field of gaseous mercury monitoring, and in particular to a semiconductor low-temperature elemental mercury generator.

BACKGROUND

In the simulation experiment, a gaseous mercury generator is required to generate a certain concentration of mercury-containing gas as a mercury source. In the related art, the gas-liquid contact area of the gaseous mercury generator is limited, the temperature is unstable, and the output gas flow rate is limited, which cannot meet the needs of production experiments.

SUMMARY

The disclosure aims at solving one of the technical problems in the related art at least to some extent. Therefore, the embodiment of the disclosure provides a semiconductor low-temperature elemental mercury generator, which has the advantages of simple operation and accurate mercury standard gas concentration.

A semiconductor low-temperature elemental mercury generator is provided, and includes a gas source and a mercury pool generating chamber. The gas source is communicated with a carrier gas pipeline and a dilution gas pipeline. The mercury pool generating chamber includes a semiconductor refrigeration device, a gas mixing device and a coil, where the coil is kept at a constant temperature through the semiconductor refrigeration device, the carrier gas pipeline is communicated with the coil, and the gas mixing device is communicated with a gas outlet of the coil and the dilution gas pipeline.

The semiconductor low-temperature elemental mercury generator according to the embodiment of the disclosure has the advantages of simple operation and accurate mercury standard gas concentration.

In some embodiments, the carrier gas pipeline is provided with a small-flow mass flowmeter, and the dilution gas pipeline is provided with a large-flow mass flowmeter.

In some embodiments, the mercury pool generating chamber is provided with an annular groove, the coil is located in the annular groove, and heat conducting liquid is filled between the coil and the groove.

In some embodiments, the coil includes an inlet section, a mercury source section and an outlet section, where quartz sand is filled in the inlet section and the outlet section, and quartz sand with mercury beads is filled in the mercury source section In some embodiments, a surface of the quartz sand in the mercury source section is coated with a gold film.

In some embodiments, a pipeline diameter of the mercury source section is greater than or equal to pipeline diameters of the inlet section and the outlet section.

In some embodiments, a length ratio of the inlet section, the mercury source section and the outlet section is (2-4):(1-3): (3-6).

In some embodiments, quartz wool is arranged at an inlet of the inlet section and an outlet of the outlet section.

In some embodiments, the semiconductor refrigeration device includes a semiconductor cooling plate and a cooling fan, and the cooling fan is located above a semiconductor cooling plate.

In some embodiments, the gas mixing device includes a tee pipe, a gas outlet of the coil and the dilution gas pipeline are respectively connected with a first end and a second end of the tee pipe, and a third end of the tee pipe is a mercury-containing standard gas outlet.

According to the disclosure, mercury vapor with standard concentration is generated by a saturated vapor pressure method, and the saturated vapor pressure of mercury is different at different temperatures. The mercury vapor with target concentration may be obtained by changing the temperature through the semiconductor refrigeration device and cooperating with the dilution gas pipeline, so that manual participation is less, the operation is simple, and the concentration accuracy of the obtained mercury-containing gas is high.

Figure 1:
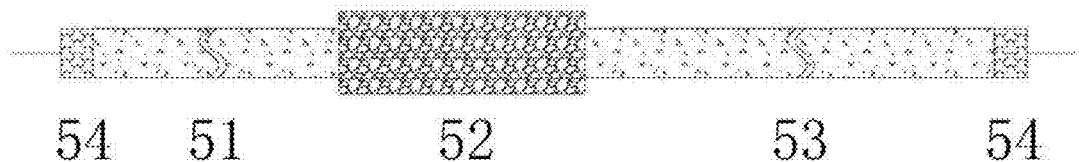
FIG. 1 is a schematic structural diagram of a semiconductor low-temperature elemental mercury generator according to an embodiment of the disclosure.

List of reference characters: 1 gas source; 2 small-flow mass flowmeter; 3 large-flow mass flowmeter; 4 mercury pool generating chamber; 5 coil; 51 inlet section; 52 mercury source section; 53 outlet section; 54 quartz wool; 6 semiconductor cooling plate; and 7 cooling fan.

DETAILED DESCRIPTION OF THE EMBODIMENTS

In the following, embodiments of the disclosure will be described in detail, examples of the embodiments are illustrated in the accompanying drawings. The embodiments described below by referring to the drawings are exemplary and are intended to explain the disclosure, but not to be construed as limiting the disclosure.

Figure 2:
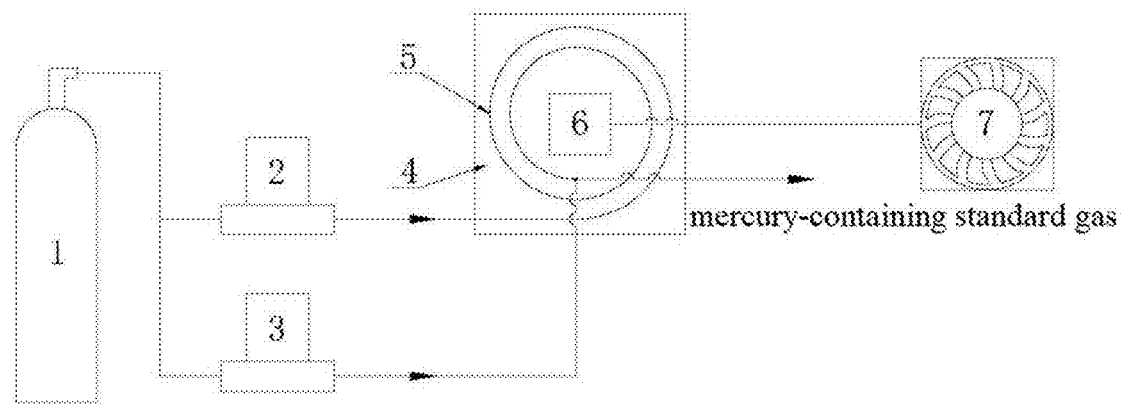
FIG. 2 is a schematic structural diagram of a coil of the semiconductor low-temperature elemental mercury generator according to an embodiment of the disclosure.

As shown in FIGS. 1 and 2, the semiconductor low-temperature elemental mercury generator according to the embodiment of the disclosure includes a gas source and 1 a mercury pool generating chamber 4, the gas source 1 is communicated with a carrier gas pipeline and a dilution gas pipeline. The mercury pool generating chamber 4 includes a semiconductor refrigeration device, a gas mixing device and a coil 5, where the coil is kept at a constant temperature through the semiconductor refrigeration device, the carrier gas pipeline is communicated with the coil 5, and the gas mixing device is communicated with a gas outlet of the coil 5 and the dilution gas pipeline. The gas source 1 uses inert gas, and the carrier gas of the carrier gas pipeline enters the mercury pool generating chamber 4 to contact with the mercury in the coil 5 to obtain saturated mercury vapor, which is mixed with dilution gas in the gas mixing device to obtain mercury-containing gas with standard concentration. The inert gas may be nitrogen. The semiconductor refrigeration device may be provided with a temperature sensor and a temperature controller to detect and control the temperature.

The semiconductor low-temperature elemental mercury generator according to the embodiment of the disclosure has the advantages of simple operation and accurate mercury standard gas concentration.

In some embodiments, as shown in FIG. 1, a small-flow mass flowmeter 2 is arranged on the carrier gas pipeline, and a large-flow mass flowmeter 3 is arranged on the dilution gas pipeline.

Specifically, the dilution gas flow rate may be set to 100-10000 times of the carrier gas flow rate. Small flow gas may ensure the gas-liquid balance between carrier gas and mercury, and large flow dilution gas may meet the gas demand of users within a large flow range.

In some embodiments, the mercury pool generating chamber 4 has an annular groove, the coil 5 is located in the annular groove, and a heat conducting liquid is filled between the coil 5 and the groove.

Specifically, the mercury pool generating chamber 4 is made of metal material with good thermal conductivity, and the annular groove is convenient for fixing the pipeline of the coil 5, which can avoid poor contact and poor heat dissipation effect caused by the twisting of the coil 5 away from the mercury pool generating chamber 4. Filling the heat conducting liquid between the coil 5 and the annular groove can increase the heat conducting area of the coil 5 and the mercury pool generating chamber 4 and ensure the heat conducting performance, and the heat conducting liquid can be heat conducting oil, which can ensure that the pipeline of the coil 5 is uniformly heated and the temperature of the semiconductor refrigeration device is consistent.

In some embodiments, as shown in FIG. 2, the coil 5 includes an inlet section 51, a mercury source section 52 and an outlet section 53, quartz sand is filled in the inlet section 51 and the outlet section 53, and quartz sand with mercury beads is filled in the mercury source section 52.

Specifically, the length of the pipeline of the coil 5 ranges from 0.5 m to 3 m, and the pipeline adopts three sections, and the inlet section 51, the mercury source section 52 and the outlet section 53 are sequentially arranged along the gas flow direction of the carrier gas. The quartz sand in the inlet section 51 can ensure that the carrier gas reaches the set temperature after entering the mercury pool generating chamber 4, and plays a preheating role. The quartz sand in the mercury source section 52 is mixed with mercury beads, the mercury content is about 1 g-5 g, and different mercury saturated vapor concentrations are formed at different set temperatures. The quartz sand in the outlet section 53 can prevent mercury beads from escaping and ensure the temperature of mercury-containing airflow to be stable at a constant value.

In some embodiments, the surface of quartz sand in the mercury source section 52 is coated with a gold film.

Specifically, coating gold film on the surface of quartz sand can improve the adsorption force of quartz sand to mercury beads and avoid mercury beads from escaping. The material of the pipeline of the coil 5 is made of materials that have no adsorption performance for mercury, such as PTFE pipe, which has the characteristics of corrosion resistance and low friction coefficient.

In some embodiments, as shown in FIG. 2, the pipeline diameter of the mercury source section 52 is greater than or equal to the pipeline diameters of the inlet section 51 and the outlet section 53.

Specifically, the diameter of the mercury source section is 5-30 mm, the pipeline diameter of the mercury source section 52 is larger than that of the inlet section 51 and the outlet section 53, and the flow speed of the carrier gas in the mercury source section 52 decreases with the increase of the diameter, so that the contact time between the carrier gas and mercury can be prolonged and the carrier gas can be better contacted with mercury.

In some embodiments, as shown in FIG. 2, the length ratio of the inlet section 51, the mercury source section 52 and the outlet section 53 is (2-4): (1-3): (3-6).

Specifically, among the lengths of inlet section 51, mercury source section 52 and outlet section 53, the length of inlet section 51 is suitable for preheating requirement, the shortest length of mercury source section 52 can reduce the volume of saturated mercury vapor, and the length of outlet section 53 can meet the requirements of constant temperature heating of mercury-containing gas flow. The length ratio of inlet section to other sections ranges from 2 to 4, the length ratio of mercury source section to other sections ranges from 1 to 3, and the length ratio of outlet section to other sections ranges from 3 to 6.

Preferably, the length ratio of the inlet section, the mercury source section and the outlet section is 3:2:5. At this time, the length of the coil is the most suitable, and the effects of the inlet section, the mercury source section and the outlet section are the best to meet the preheating requirement and heating requirement.

In some embodiments, as shown in FIG. 2, quartz wool 54 is arranged at the inlet of the inlet section 51 and the outlet of the outlet section 53.

Specifically, quartz wool 54 is blocked at both ends of the coil 5 to avoid quartz sand leakage and ensure the quantity of quartz sand. The mesh number of the Quartz sand is 20~100 mesh.

In some embodiments, as shown in FIG. 1, the semiconductor refrigeration device includes a semiconductor cooling plate 6 and a cooling fan 7, and the cooling fan 7 is located above the semiconductor cooling plate 6.

Specifically, the cooling fan 7 is connected with and dissipates heat for the semiconductor cooling plate 6, the cold surface of the semiconductor cooling plate 6 is in contact with the mercury pool generating chamber 4, the temperature control range of the semiconductor cooling plate 6 is minus 10-50° C., and the temperature control accuracy is <0.02° C. The semiconductor refrigeration device adjusts and maintains the internal temperature of the mercury pool generating chamber 4 through the semiconductor cooling plate 6, and the outside of the mercury pool generating chamber 4 is sleeved with heat insulation materials to realize the constant internal temperature.

In some embodiments, the gas mixing device includes a tee pipe, the gas outlet and the dilution gas pipeline of the coil 5 are respectively connected with the first end and the second end of the tee pipe, and the third end of the tee pipe is a mercury-containing standard gas outlet.

Specifically, the gas mixing device can also include a gas mixing cavity, the third end of the tee pipe is communicated with the gas mixing cavity, and the mercury-containing carrier gas and the dilution gas are mixed in the gas mixing cavity to form mercury-containing gas with standard concentration.

In Embodiment 1, N2 is used as the gas source 1, the temperature of the mercury pool generating chamber 4 is controlled at 10° C., the total length of the pipeline of the coil 5 is 2 m, and the length ratio of the quartz sand in the inlet section 51, the quartz sand mixed with mercury beads and the quartz sand in the outlet section 53 is 3:2:5. The theoretical value of the output concentration converted to standard temperature and pressure at 0° C. is 5.74 μg/m3, and the measured average value is 5.77 μg/m3, a relative deviation is 0.5%.

In Embodiment 2, N2 is used as the gas source 1, the temperature of the mercury pool generating chamber 4 is controlled at 15° C., the total length of the pipeline of the coil 5 is 2 m, and the length ratio of the quartz sand in the inlet section 51, the quartz sand mixed with mercury beads and the quartz sand in the outlet section 53 is 3:2:5. The theoretical value of the output concentration converted to standard temperature and pressure at 0° C. is 18.13 μg/m3, and the measured average value is 17.88 μg/m3, a relative deviation is −1.4%.

In the description of the disclosure, it should be understood that the azimuth or positional relationship indicated by the terms "center", "longitudinal direction", "transverse direction", "length", "width", "thickness", "up", "down", "front", "back", "left", "right", "vertical" and "horizontal", "top", "bottom", "inside", "outside", "clockwise", "counterclockwise", "axial", "radial" and "circumferential" etc. is based on the azimuth or positional relationship shown in the attached drawings, only for the convenience of describing the disclosure and simplifying the description, and does not indicate or imply that the referred device or element must have a specific orientation, be constructed and operated in a specific orientation, so it cannot be understood as a limitation of the disclosure.

In addition, the terms "first" and "second" are only used for descriptive purposes, and cannot be understood as indicating or implying relative importance or implicitly indicating the number of indicated technical features. Therefore, the features defined as "first" and "second" can explicitly or implicitly include at least one of these features. In the description of the disclosure, "multiple" means at least two, such as two, three, etc., unless otherwise specifically defined.

In the disclosure, unless otherwise specified and limited, the terms "installation", "connection", "connecting" and "fixation" should be broadly understood, for example, a fixed connection, a detachable connection or an integrated connection may be used. It can be mechanically connected, electrically connected or communicated with each other. It can be directly connected or indirectly connected through an intermediary, and it can be the internal connection of two elements or the interaction between two elements, unless otherwise specified. For those skilled in the art, the specific meanings of the above terms in the disclosure can be understood according to specific situations.

In the disclosure, unless otherwise specified and limited, the first feature "above" or "below" the second feature may be the direct contact between the first and second features, or the indirect contact between the first and second features through an intermediary. Moreover, the first feature is "above", "up" and "on" the second feature, which can mean that the first feature is directly above or obliquely above the second feature, or just means that the horizontal height of the first feature is higher than the second feature. The words "under", "down" and "below" of the first feature can mean that the first feature is directly or obliquely below the second feature, or just mean that the horizontal height of the first feature is smaller than the second feature.

In the disclosure, the terms "one embodiment", "some embodiments", "examples", "specific examples" or "some examples" etc. mean that the specific features, structures, materials or characteristics described in connection with this embodiment or example are included in at least one embodiment or example of the disclosure. In this specification, the schematic expressions of the above terms are not necessarily aimed at the same embodiment or example. Moreover, the specific features, structures, materials or characteristics described may be combined in any one or more embodiments or examples in a suitable manner. In addition, those skilled in the art can combine and unite different embodiments or examples and features of different embodiments or examples described in this specification without contradicting each other.

Although the embodiments of the disclosure have been shown and described above, it can be understood that the above-mentioned embodiments are exemplary and cannot be understood as limitations of the disclosure, and the changes, modifications, substitutions and variations made to the above-mentioned embodiments by ordinary skilled in the field are within the scope of protection of the disclosure.

What is claimed is:

1. A semiconductor low-temperature elemental mercury generator, comprising:
    a gas source, communicated with a carrier gas pipeline and a dilution gas pipeline, and
    a mercury pool generating chamber, wherein the mercury pool generating chamber comprises a semiconductor refrigeration device, a gas mixing device and a coil, wherein the coil is kept at a constant temperature through the semiconductor refrigeration device, the carrier gas pipeline is communicated with the coil, and the gas mixing device is communicated with a gas outlet of the coil and the dilution gas pipeline;
    wherein the mercury pool generating chamber is provided with an annular groove, the coil is located in the annular groove, and heat conducting liquid is filled between the coil and the groove;
    the mercury pool generating chamber is made of metal material with good thermal conductivity;
    the coil comprises an inlet section, a mercury source section and an outlet section, wherein quartz sand is filled in the inlet section and the outlet section, and quartz sand with mercury beads is filled in the mercury source section;
    a surface of the quartz sand in the mercury source section is coated with a gold film.

2. The semiconductor low-temperature elemental mercury generator according to claim 1, wherein the carrier gas pipeline is provided with a small-flow mass flowmeter, and the dilution gas pipeline is provided with a large-flow mass flowmeter.

3. The semiconductor low-temperature elemental mercury generator according to claim 1, wherein a pipeline diameter of the mercury source section is greater than or equal to pipeline diameters of the inlet section and the outlet section.

4. The semiconductor low-temperature elemental mercury generator according to claim 1, wherein a length ratio of the inlet section, the mercury source section and the outlet section is (2-4): (1-3): (3-6).

5. The semiconductor low-temperature elemental mercury generator according to claim 1, wherein quartz wool is arranged at an inlet of the inlet section and an outlet of the outlet section.

6. The semiconductor low-temperature elemental mercury generator according to claim 1, wherein the semiconductor refrigeration device comprises a semiconductor cooling plate and a cooling fan, and the cooling fan is located above the semiconductor cooling plate.

7. The semiconductor low-temperature elemental mercury generator according to claim 1, wherein the gas mixing device comprises a tee pipe, a gas outlet of the coil and the dilution gas pipeline are respectively connected with a first end and a second end of the tee pipe, and a third end of the tee pipe is a mercury-containing standard gas outlet.

* * * * *